US010156718B2

United States Patent
Koenig et al.

(10) Patent No.: US 10,156,718 B2
(45) Date of Patent: Dec. 18, 2018

(54) PROTECTION GLASS ADAPTER FOR A SURGICAL MICROSCOPE

(71) Applicant: Carl Zeiss Meditec AG, Jena (DE)

(72) Inventors: Frank Koenig, Aalen (DE); Daniel Lindner, Koenigsbronn (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/376,300

(22) Filed: Dec. 12, 2016

(65) Prior Publication Data

US 2017/0168292 A1 Jun. 15, 2017

(30) Foreign Application Priority Data

Dec. 11, 2015 (DE) .......................... 10 2015 225 009

(51) Int. Cl.
*A61B 17/00* (2006.01)
*A61B 46/10* (2016.01)
(Continued)

(52) U.S. Cl.
CPC .......... *G02B 27/0006* (2013.01); *A61B 46/10* (2016.02); *A61B 90/20* (2016.02);
(Continued)

(58) Field of Classification Search
CPC ................ G02B 27/0006; G02B 21/02; G02B 21/0012; G02B 21/0008; G02B 21/362; G02B 27/0176
(Continued)

(56) References Cited

U.S. PATENT DOCUMENTS 3,528,720 A 9/1970 Treace
5,467,223 A * 11/1995 Cleveland, Jr. .... G02B 21/0012
359/510
(Continued)

FOREIGN PATENT DOCUMENTS

DE 44 13 920 A1 12/1994
DE 10 2007 043 995 A1 4/2009
WO 2009/037082 A2 3/2009

OTHER PUBLICATIONS

European Search Report dated Apr. 21, 2017 of corresponding European Patent Application 16199724.2 and English translation thereof.
(Continued)

*Primary Examiner* — Jade R Chwasz
(74) *Attorney, Agent, or Firm* — Walter Ottesen, P.A.

(57) ABSTRACT

A protection glass adapter for a surgical microscope has a first abutment surface which can be brought into contact with a corresponding second abutment surface of the microscope. The adapter has a guide opening for receiving a main objective. The guide opening is a truncated cone with a central axis. The greater diameter of the truncated cone is formed toward the first abutment surface. A positioning element of the adapter is rigid and arranged on the first abutment surface. The positioning element is received with form-fit engagement in a mating element on the surgical microscope. The adapter has a holding element. A holding force in the form of a magnetic force can be applied by the holding element parallel to the central axis between the adapter and the microscope.

15 Claims, 3 Drawing Sheets

(51) Int. Cl.
    *A61B 90/20*     (2016.01)
    *G02B 21/00*     (2006.01)
    *G02B 21/02*     (2006.01)
    *G02B 23/16*     (2006.01)
    *G02B 27/00*     (2006.01)

(52) U.S. Cl.
    CPC ......... *G02B 21/0012* (2013.01); *G02B 21/02* (2013.01); *A61B 2017/00477* (2013.01); *A61B 2017/00876* (2013.01); *G02B 23/16* (2013.01)

(58) Field of Classification Search
    USPC ................. 359/507, 510, 511, 512, 513, 514
    See application file for complete search history.

(56) References Cited

U.S. PATENT DOCUMENTS

| | | |
|---|---|---|
| 5,608,574 A | 3/1997 | Heinrich |
| 5,682,264 A | 10/1997 | Cleveland |
| 6,318,864 B1 * | 11/2001 | Fukaya .............. G02B 21/0012 359/368 |
| 2005/0063058 A1 | 3/2005 | Langley |
| 2005/0094269 A1 | 5/2005 | Moses et al. |
| 2010/0238551 A1 | 9/2010 | Hubbs |

OTHER PUBLICATIONS

English translation of the Office action of the German Patent Office dated Jul. 28, 2016 in German patent application 10 2015225009.1 on which the claim of priority is based.

\* cited by examiner

PROTECTION GLASS ADAPTER FOR A SURGICAL MICROSCOPE

CROSS REFERENCE TO RELATED APPLICATION

This application claims priority of German patent application no. 10 2015 225 009.1, filed Dec. 11, 2015, the entire content of which is incorporated herein by reference.

FIELD OF THE INVENTION

The invention relates to a protection glass adapter for a surgical microscope.

BACKGROUND OF THE INVENTION

In order to protect the main objective of a surgical microscope from contamination during an operation, it is possible to arrange a protection glass module in front of the main objective. The protection glass module includes a protection glass adapter and an objective protection glass. The protection glass adapter is connected mechanically to the surgical microscope. The objective protection glass is arranged on the protection glass adapter, such that an operating site can be viewed through the main objective and the objective protection glass. In addition, the protection glass adapter can be connected to a sterile cover film in order to protect the entire surgical microscope from contamination during an operation.

DE 10 2007 043 995 A1 discloses a protection glass adapter, designated there as a mountable protection glass frame, for a surgical microscope. During the mounting of the protection glass frame, lateral guide tabs ensure guiding contact with the surgical microscope. Thereafter, latching pins engage in receiving bores, and a lug engages in the recesses provided for it. The exact positioning of the protection glass frame is obtained when resilient pressure pins, which are mounted in the receiving bores perpendicularly with respect to the mounting direction, latch into the respective narrowed zone of the latching pins.

When this protection glass frame is mounted, there is a relatively large contact surface and, by association, relatively great friction between surgical microscope and protection glass adapter. When the latching pins engage in the receiving bores and resilient pressure pins are moved counter to the spring force, the force that has to be applied to be able to arrange the protection glass adapter on the surgical microscope increases. These forces may mean that the surgical microscope has to be held in order to ensure that its position does not change during the mounting of the protection glass adapter.

SUMMARY OF THE INVENTION

It is therefore an object of the invention to make available a protection glass adapter for a surgical microscope, which protection glass adapter can be mounted very easily and with very little friction onto on a surgical microscope, without the surgical microscope having to be held while doing this.

According to the invention, the protection glass adapter for a surgical microscope has a first abutment surface, wherein the first abutment surface is configured in such a way that it can be brought into contact with a corresponding second abutment surface of the surgical microscope. The protection glass adapter has a guide opening for receiving a main objective of the surgical microscope, wherein the guide opening is configured as a truncated cone with a first central axis, wherein the greater diameter of the truncated cone is formed toward the first abutment surface. The protection glass adapter has at least one positioning element, wherein the at least one positioning element is rigid and is arranged on the first abutment surface or on the surface of the guide opening, wherein the positioning element is suitable for being received with form-fit engagement in a mating element on the surgical microscope. The protection glass adapter has at least one holding element, wherein a holding force can be applied by the holding element parallel to the first central axis between the protection glass adapter and the surgical microscope, wherein the holding force is formed by a magnetic force.

The protection glass adapter according to the invention can be very easily mounted on a surgical microscope. A surgical microscope has a main objective with an optical axis.

The guide opening of the protection glass adapter is configured as a truncated cone with a first central axis. In this way, the protection glass adapter can be very easily pushed over the main objective. As a result of the large diameter, there is at first a very great clearance between the main objective and the protection glass adapter. This position of the protection glass adapter can thus be easily sensed by the user without looking. During the movement of the protection glass adapter in the direction of the optical axis to the second abutment surface on the surgical microscope, the protection glass adapter is centered and guided by the cone shape of the guide opening.

While this is being done, there is barely any friction between the protection glass adapter and the main objective. The friction surface is limited to a point contact or a thin line contact. The protection glass adapter can be very easily guided with an exact fit toward the second abutment surface and onto the surgical microscope without any appreciable force having to be exerted on the surgical microscope.

The positioning element arranged on the first abutment surface additionally has the effect that the first abutment surface of the protection glass adapter is not yet in contact over a large surface area with the corresponding second abutment surface of the surgical microscope. Rather, there is only a very slight friction between the very small contact surface of the positioning element and the second abutment surface of the surgical microscope. The configuration of the guide surface as a truncated cone additionally has the effect that there is still a certain clearance between the protection glass adapter and the main objective, such that the friction between protection glass adapter and main objective is still limited to a point contact or line contact. Via gentle left/right movements of the protection glass adapter, the positioning element slides into a corresponding mating element of the surgical microscope. The distance between the two contact surfaces of the protection glass adapter and of the surgical microscope thereby decreases. At this position, the magnetic holding force is very considerable, and the protection glass adapter is held at this position exclusively by a magnetic holding force. It is only in this position that the clearance between the surface of the guide opening, configured as a truncated cone, and the main objective is minimal, such that the protection glass adapter is arranged with a precise fit and in a correct position on the main objective.

The ease with which the protection glass adapter is mounted on a surgical microscope will be further illustrated by the following kinematic considerations.

The optical axis of the main objective defines a Z axis. An X-Y plane is formed perpendicularly with respect to this Z axis. When the protection glass adapter is guided over the main objective and the first abutment surface is not in contact with the corresponding second abutment surface, the protection glass adapter is slidable in the X-Y plane and tiltable with respect to the X-Y plane in accordance with the clearance formed between guide opening and main objective. Moreover, the protection glass adapter is freely rotatable about the central axis of the guide opening, which is guided substantially parallel to the optical axis.

It is only when the first abutment surface of the protection glass adapter is in form-fit engagement with the corresponding second abutment surface of the surgical microscope that the protection glass adapter is oriented in a plane parallel to the first abutment surface. The guide opening has the effect that, except for the remaining slight residual clearance between the guide opening and the main objective in this position, the protection glass adapter is fixed in the X-Y plane. In this position, the positioning element is received with form-fit engagement in the mating element on the surgical microscope and fixes the protection glass adapter in the direction of rotation with respect to the central axis or the Z axis. The position of the protection glass adapter with respect to the surgical microscope is thus clearly defined with respect to all degrees of freedom. Only in this position does the holding element effect a magnetic holding force between the protection glass adapter and the surgical microscope.

The correct position of the protection glass adapter can thus be sensed very quickly and easily. The protection glass adapter can be secured on the main objective very quickly and easily with one hand, without any appreciable friction or force being exerted on the surgical microscope thereby. Therefore, it is also not necessary to hold the surgical microscope with the other hand. Moreover, this connection can be very easily released again at any time.

Alternatively, an arrangement of the at least one positioning element on the surface of the guide opening is conceivable. In this arrangement, the at least one corresponding mating element can be formed on the main objective of the surgical microscope.

In an embodiment of the invention, the at least one positioning element has a hemispherical shape.

A hemispherical positioning element can be very easily inserted with form-fit engagement into a corresponding mating element even in the event of slight tilting of the protection glass adapter. When the positioning element is in contact with the complementary abutment surface of the surgical microscope at a position outside the mating element, the semicircular shape means that the contact surface is only at a small point. A further advantage is that, by virtue of the hemispherical surface, the protection glass adapter can be more easily rotated out of the mating element by lateral rotation about the central axis.

In an embodiment of the invention, two positioning elements are arranged on the first abutment surface or on the surface of the guide opening.

Via two positioning elements, an unambiguous position of the protection glass adapter on the surgical microscope is defined even when there is a substantial clearance between the guide opening and the main objective. Moreover, a tilting of the central axis of the protection glass adapter can be more easily sensed if the two positioning elements are in contact with the complementary second abutment surface of the surgical microscope.

In an embodiment of the invention, three positioning elements are arranged on the first abutment surface or on the surface of the guide opening.

When the positioning element is in contact with the complementary second abutment surface of the surgical microscope at a position outside the mating elements, this contact surface is formed by three contact points. A tilting of the central axis of the protection glass adapter in this contact position can thus be reliably avoided. When the three positioning elements are arranged on the surface of the guide opening, the outer surface of the main objective can form the contact surface of the surgical microscope.

In an embodiment of the invention, at least two holding elements are arranged on the protection glass adapter.

A better holding action is advantageously obtainable via at least two holding elements. The two holding elements are advantageously configured as magnetic holding elements.

In an embodiment of the invention, the guide opening has a cone angle of between 10° and 45°, preferably between 10° and 20°.

By means of the cone shape of the guide opening, it is possible to obtain a relatively large clearance, and therefore practically no friction or only minimal friction, between the protection glass adapter and the main objective of the surgical microscope. This clearance is minimal only at the moment when the first abutment surface of the protection glass adapter is in form-fit engagement with the second abutment surface of the surgical microscope.

In an embodiment of the invention, the protection glass adapter includes an objective protection glass.

In this way, a complete protection glass module can advantageously be made available. The same advantages as for the protection glass adapter can be obtained for the protection glass module including a protection glass adapter and an objective protection glass.

In an embodiment of the invention, the objective protection glass is separably connected to the protection glass adapter and is received in a receiving device.

In this way, the objective protection glass, for example if contaminated, can advantageously be replaced without having to remove the protection glass adapter from a surgical microscope.

In an embodiment of the invention, a microscope drape is arranged on the protection glass adapter.

The microscope drape, a flexible cover film, can be used to cover the surgical microscope. The protection glass adapter can advantageously be mounted on the surgical microscope with one hand, while the microscope drape can be held with the other hand. The overall system including protection glass adapter and microscope drape is therefore very easy to handle. Moreover, a particularly good seal between microscope drape and surgical microscope can be obtained by virtue of the guide opening and/or the abutment surface of the protection glass adapter.

In an embodiment of the invention, the microscope drape is arranged on the first abutment surface.

This connection can thus be produced very easily. Moreover, a particularly good seal between microscope drape and surgical microscope can be obtained in the area of the protection glass adapter.

A surgical microscope advantageously includes a protection glass adapter as described above. The surgical microscope has a second abutment surface, which can be brought into contact with the first abutment surface of the protection glass adapter. The surgical microscope has a main objective with an outer circumferential surface, wherein the outer circumferential surface is configured as a truncated cone, wherein the greater diameter of the truncated cone is formed toward the second abutment surface. The surgical microscope has at least one mating element which, in position and shape, can be brought into form-fit engagement with the at least one positioning element. The surgical microscope has at least one mating holding element, which is configured in such a way that a magnetic holding force can be effected between the at least one holding element and the at least one mating holding element.

The protection glass adapter can be very quickly centered and guided over the main objective and mounted on the surgical microscope, without having to hold the surgical microscope. The above-described advantages can thus be achieved. By virtue of the compact arrangement of the protection glass adapter on the surgical microscope, the protection glass adapter can advantageously be mounted on a surgical microscope in such a way that the work space between surgical microscope and operating site is restricted only slightly.

In an embodiment of the invention, a surgical microscope includes a protection glass adapter, wherein the guide opening of the protection glass adapter is guided over the main objective. The protection glass adapter is movable in a rotary motion about the central axis when the at least one positioning element is in contact with the second abutment surface, such that the first abutment surface is arranged by the positioning element at a distance from the second abutment surface of the surgical microscope when the positioning element is not positioned in form-fit engagement with the mating element. The holding force between the at least one holding element and the at least one mating holding element is formed exclusively at a first position at which the positioning element is positioned at a predetermined position in relation to the surgical microscope and the positioning element is arranged in form-fit engagement in the mating element in relation to the surgical microscope, such that the first abutment surface is in contact with the corresponding second abutment surface of the surgical microscope exclusively at the first position.

Thus, the protection glass adapter can advantageously be mounted very easily on the surgical microscope.

In an embodiment of the invention, the receiving device of the protection glass adapter has at least one latching device for the objective protection glass.

The releasable latching device ensures that the objective protection glass is held securely in the receiving device of the protection glass adapter during use and yet is connected separably to the protection glass adapter.

In an embodiment of the invention, the protection glass adapter is formed in one piece with the objective protection glass.

In this way, the protection glass module can be produced more cost-effectively, since a special receiving device on the protection glass adapter for the objective protection glass is dispensed with. A reduction in weight of the protection glass adapter can thus be achieved.

In an embodiment of the invention, the protection glass adapter is configured as a ring.

This permits more cost-effective production of the tools that are used to produce a protection glass adapter made of plastic.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
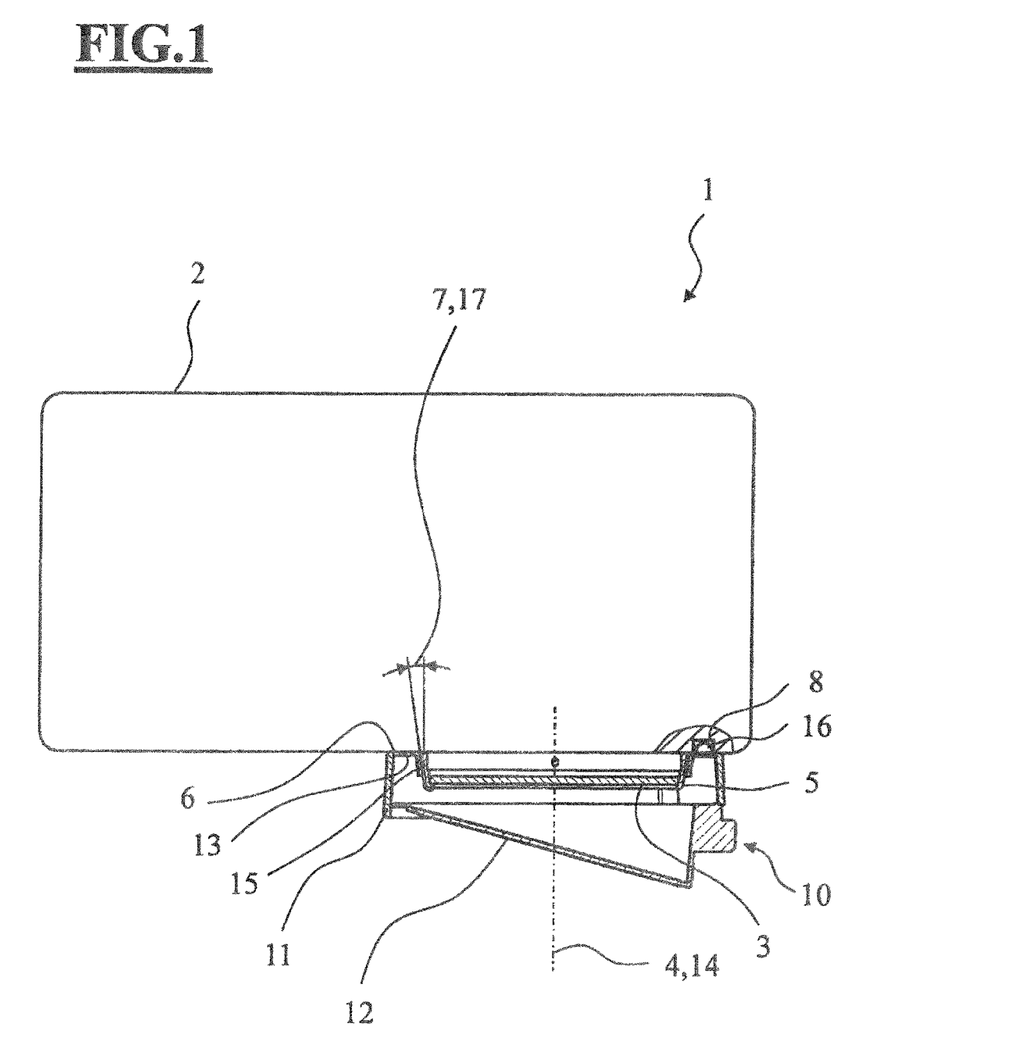
FIG. 1 shows a schematic cross-sectional view of a surgical microscope with a protection glass module.

FIG. 1 shows a schematic view of a surgical microscope with a protection glass module.

A surgical microscope system 1 includes a surgical microscope 2 with a protection glass module 10. The surgical microscope 2 has a main objective 3 with an optical axis 4. The outer form of the main objective 3 is configured as a truncated cone with a second cone angle 7 and with an outer circumferential surface 5. The greater diameter of the truncated cone points toward the surgical microscope 2.

The protection glass module 10 is arranged on the underside of the surgical microscope 2. The protection glass module 10 includes a protection glass adapter 11 and an objective protection glass 12. A first abutment surface 13 of the protection glass module 10 is thereby in contact with a corresponding second abutment surface 6 of the surgical microscope. The protection glass module 10 is arranged separably on the surgical microscope 2. The objective protection glass 12 is separably connected to the protection glass adapter 11.

The protection glass adapter 11 has a guide opening 15 for receiving the main objective 3. The guide opening 15 is configured as a truncated cone with a first cone angle 17 and with a first central axis 14. The greater diameter of the truncated cone is formed toward the first abutment surface 13. The first cone angle 17 of the guide opening 15 has the same magnitude as the second cone angle 7 of the outer circumferential surface 5 of the main objective 3. The central axis 14 is coincident with the optical axis 4 of the main objective 3. The objective protection glass 12 is arranged at an angle of greater or less than 90° with respect to the optical axis 14, in order to avoid reflections in the microscope lens system including the main objective 3. The defined inclination of the objective protection glass permits a reflection-free view of an operating site.

A first positioning element 16 is arranged on the first abutment surface 13. The first positioning element 16 is configured rigidly as a hemisphere. The second abutment surface 6 of the surgical microscope 2 has a first mating element 8, which is configured as a recess or bore. The first positioning element 16 thereby engages with a form-fit in the first mating element 8 when the first abutment surface 13 is in contact with the second abutment surface 6, such that the protection glass adapter 11 is positioned exactly with respect to the main objective 3. The form-fit engagement is such that the first positioning element 16 is positioned with a contact line in form-fit engagement in the mating element 8. The first positioning element 16 can be configured as a hemisphere, and the mating element 8 can be configured as a bore. The contact line can be a circle line on the hemisphere.

In this position, the protection glass adapter 10 is held on the surgical microscope by a holding force. The holding force is formed exclusively by a magnetic force. For this purpose, holding elements (not shown) are arranged on the protection glass adapter 10 and can form a magnetic force with corresponding magnetic mating holding elements (not shown) on the surgical microscope. The holding force is formed parallel to the first central axis 14 between the protection glass adapter 10 and the surgical microscope 2. The holding elements or mating holding elements can include permanent magnets in combination with other magnets or ferromagnetic metals, for example iron. For reasons relating to cost, the holding elements arranged on the protection glass adapter preferably include iron. The magnets on the surgical microscope 2 can also be configured as electromagnets.

Alternatively, it is conceivable that the holding force is formed by a frictional force and/or adhesive force or a combination of frictional force and/or adhesive force and magnetic force.

The cone angle of the guide opening 15 can be in a range of between 1° and 45°; preferred values are, for example 10° or 15°. It is even conceivable that the guide opening 15 is in a concave or convex shape. It is also conceivable that the outer form of the main objective 3 forms a concave or convex outer shape.

The protection glass adapter 11 and/or the objective protection glass 12 can be made of plastic. It is also conceivable that the protection glass adapter 11 is configured in one piece together with the objective protection glass 12. The objective protection glass 12 is transparent.

It is also conceivable that the first positioning element 16 and the first mating element 8 are each of inverted configuration, that is, the first positioning element 16 is formed as a recess or as a hole and the first mating element is formed as a hemisphere arranged on the second abutment surface 6, which hemisphere can engage with a form-fit in the recess or the hole.

Figure 2:
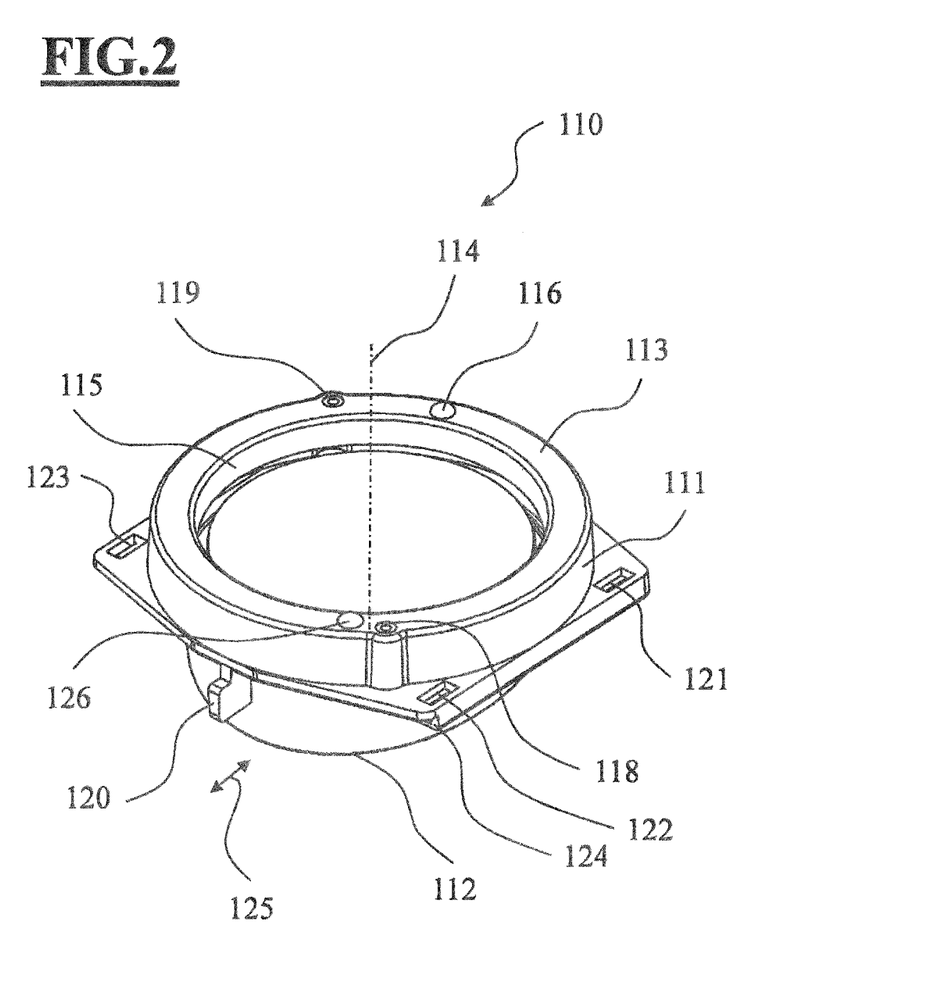
FIG. 2 shows a view of a first embodiment of a protection glass adapter according to the invention with a protection glass.

FIG. 2 shows a view of a first embodiment of a protection glass adapter 111 according to the invention with an objective protection glass 112.

A protection glass module 110 has the same components as the protection glass module 10 as per FIG. 1. The reference signs are in each case increased by one hundred in relation to the protection glass module 10.

The protection glass module 110 includes the protection glass adapter 111 and the objective protection glass 112. The objective protection glass 112 is transparent.

The protection glass module includes a first abutment surface 113, which is configured as a plane surface. A guide opening 115 is configured as a truncated cone with a central axis 114. The greater diameter of the truncated cone is formed toward the first abutment surface 113.

A first positioning element 116 and a second positioning element 126 are arranged on the first abutment surface 113. The first positioning element 116 and the second positioning element 126 are each configured rigidly as hemispheres. The center point of the two hemispheres is in each case defined under the abutment surface 113, such that the height of the two hemispheres is smaller than the respective radius. This has the effect that, at the transition between the abutment surface 113 and the first positioning element 116 or the second positioning element 126, an angle is in each case formed that is greater than 90°. This facilitates the release of the protection glass module 110 from a surgical microscope when the protection glass module 110 is rotated about the central axis 114. The center points of the first positioning element 116 and of the second positioning element 126 in this case do not lie exactly opposite each other, with respect to the central axis 114, so as to avoid the protection glass adapter being mountable on the surgical microscope at two different positions with respect to the central axis 114.

A first holding element 118 and a second holding element 119 are arranged on the first abutment surface 113. The holding elements 118, 119 can be arranged flush on the first abutment surface 113 or can be introduced into the protection glass adapter at a short distance, for example 0.3 mm, below the first abutment surface 113. The first holding element 118 and the second holding element 119 have the effect that a magnetic holding force can be formed between the protection glass adapter 111 and the surgical microscope, which force is sufficient to hold the protection glass adapter 111 securely on the surgical microscope. For this purpose, the holding elements 118, 119 can be configured as permanent magnets, wherein the associated holding elements on the surgical microscope likewise include permanent magnets, electric magnets or ferromagnetic metals, for example, iron. It is also conceivable that the holding elements 118, 119 include iron and the associated holding elements on the surgical microscope form permanent magnets, preferably neodymium magnets or electric magnets. The holding elements 118, 119 can be pressed in, bonded in or cast together with the protection glass adapter. The holding elements can be introduced into the protection glass adapter from the front, that is, from the abutment surface 113, or from the rear side.

It is also conceivable that the positioning elements 116, 126 are configured as holding elements that are able to effect a magnetic holding force.

The objective protection glass 112 is guided in a receiving device, a guide rail 124, and is held by four latching elements.

FIG. 2 shows a first latching element 121, a second latching element 122 and a third latching element 123. The objective protection glass has a handle 120. When the latching action of the latching elements 121, 122, 123 is overcome, the handle 120 can be used to move the objective protection glass 120 in the guide rail 124, as indicated by the first double arrow 125. In this way, the protection glass adapter 111 and the objective protection glass 112 are connected separably to each other. It is also conceivable that the latching elements are configured as laterally arranged latching hooks which, for example, can be actuated by a thumb and a finger.

The objective protection glass 112 is made of a transparent material, preferably plastic. The underside of the objective protection glass is inclined by an angle, preferably of 15°, with respect to a plane orthogonal to the central axis 114. The objective protection glass 112 is thus configured in such a way that an operating site can be viewed almost without restriction. Possible disruptive reflections are largely avoided by the inclined position of the objective protection glass. The protection glass adapter 111 and the objective protection glass 112 are sterilizable.

Figure 3:
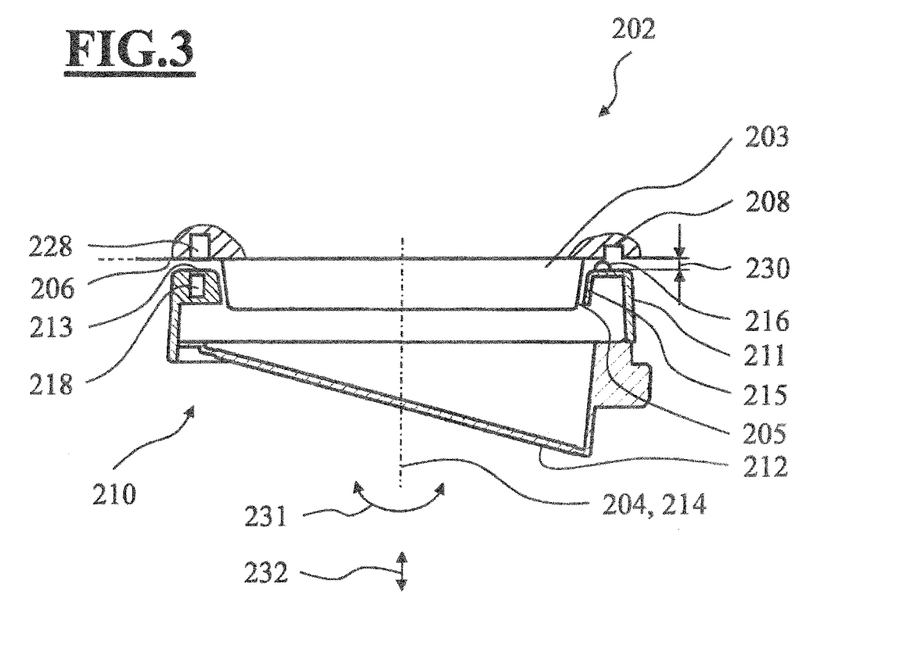
FIG. 3 shows a schematic cross-sectional view of a protection glass adapter, which is guided over a main objective; and, FIG. 4 shows a schematic view of a protection glass adapter according to FIG. 3, which is arranged on a surgical microscope.

FIG. 3 shows a schematic cross-sectional view of a protection glass adapter, which is guided over a main objective.

A protection glass module 210 according to FIG. 3 has the same components as the protection glass module 110 as per FIG. 2.

The reference signs are in each case increased by one hundred in relation to the protection glass module 110.

The protection glass module 210 includes a protection glass adapter 211 with an objective protection glass 212. The protection glass adapter 211 is guided over a main objective 203. The main objective 203 has an optical axis 204 and a conical outer circumferential surface 205.

A first abutment surface 213 of the protection glass adapter has a distance 230 from a second abutment surface 206 of a surgical microscope 202. A relatively large clearance is formed between the outer circumferential surface 205 of the main objective 203 and the conical guide opening 215 of the protection glass adapter with a central axis 214. The protection glass adapter 211 is freely movable and therefore very easily rotatable about the central axis 214, as indicated by the second double arrow 231, and can slide along the central axis 214, as indicated by the third double arrow 232.

A first positioning element 216 touches the second abutment surface 206 at a single point. The friction between protection glass adapter 211 and surgical microscope is thus minimal. A second or third positioning element (not shown) can be arranged on the protection glass adapter. The contact points between second positioning element and third positioning element also mean that the friction between protection glass adapter and surgical microscope is minimal. Even in the event of the protection glass adapter 211 tilting about the optical axis 204, the friction is restricted to the point contact and/or line contact between protection glass adapter 216 and surgical microscope 202. In this position, there is no holding force formed between the first holding element 218, a ferromagnetic iron element, and a first mating holding element 228, a permanent magnet.

Figure 4:
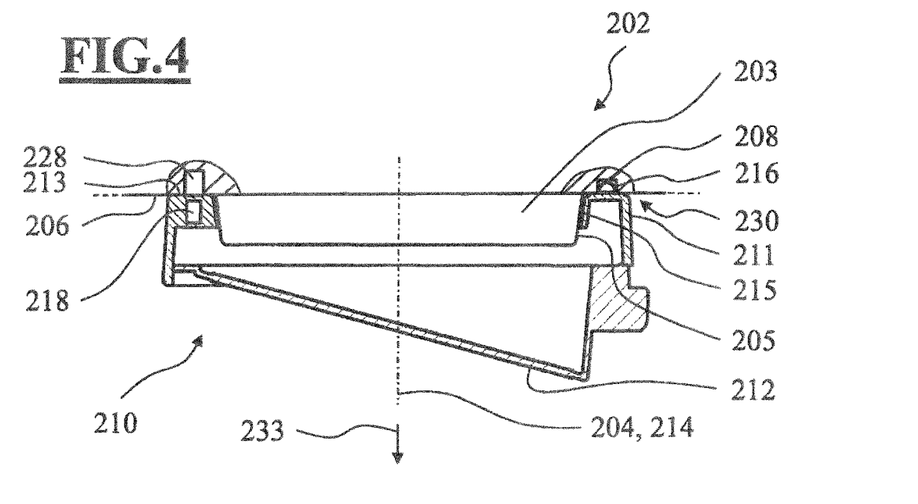

Via a slight rotation movement of the protection glass adapter 211, the first positioning element 216 slides into the corresponding first mating element 208 of the surgical microscope. This position is shown in FIG. 4. This movement is supported by the increasing magnetic holding force that develops there.

FIG. 4 shows a schematic view of a protection glass adapter according to FIG. 3, which is arranged on a surgical microscope.

The protection glass module 210 according to FIG. 4 has the same components as the protection glass module 110 as per FIG. 3.

At this position, the second abutment surface 206 of the surgical microscope 202 is in contact with the first abutment surface 213 of the protection glass adapter 211. The first positioning element 216 is arranged in the corresponding first mating element 208, a bore. The contact line between the positioning element 216 and the mating element 208 can form a circle line.

In this position, the maximum magnetic holding force is formed between the first holding element 218, a ferromagnetic iron element, and the first mating holding element 228, a permanent magnet. A second holding element (not shown in FIG. 3 and FIG. 4) can also be present on the protection glass adapter 211, and a corresponding fourth holding element (not shown) can be present on the surgical microscope 202. An even stronger holding force can thus be obtained between protection glass adapter 211 and surgical microscope 202.

To release the protection glass adapter 211 from the surgical microscope 202, the protection glass adapter 211 is rotated easily about the central axis 114. The first positioning element 216 thus slides out of the corresponding first mating element 208, and the distance between the first abutment surface 213 and the second abutment surface 206 is increased. The first holding element 218 and the first mating holding element 228 are no longer flush and, as a result of the rotation, have an offset in relation to each other. In combination with the increased distance between the holding elements, the magnetic holding force decreases almost to zero. The protection glass adapter can thus be very easily removed again from the surgical microscope 202.

The aforementioned configurations apply in the same way to a protection glass adapter 211 with or without an objective protection glass 212.

It is understood that the foregoing description is that of the preferred embodiments of the invention and that various changes and modifications may be made thereto without departing from the spirit and scope of the invention as defined in the appended claims.

LIST OF REFERENCE SIGNS 1 surgical microscope with protection glass module
2 surgical microscope
3, 203 main objective
4, 204 optical axis
5, 205 outer circumferential surface
6, 206 second abutment surface
7 second cone angle
8, 208 first mating element
10, 110, 210 protection glass module
11, 111, 211 protection glass adapter
12, 112, 212 objective protection glass
13, 113, 213 first abutment surface
14, 114, 214 central axis
15, 115, 215 guide opening
16, 116, 216 first positioning element
17 first cone angle
118, 218 first holding element
119 second holding element
120 handle
121 first latching element
122 second latching element
123 third latching element
124 guide rail
125 first double arrow (sliding direction)
126 second positioning element
228 third holding element
230 distance
231 second double arrow (rotation direction)
232 third double arrow (sliding direction)
233 arrow (sliding direction)

What is claimed is:

1. A protection glass adapter for a surgical microscope having a main objective configured as a first truncated cone defining a greater diameter directed toward the surgical microscope, the protection glass adapter comprising:
   an adapter body having a first abutment surface configured to be brought into contact with a corresponding second abutment surface of the surgical microscope;
   said adapter body defining a guide opening configured to receive the main objective of the surgical microscope;
   said guide opening having a guide opening surface and being adapted as a second truncated cone with a first central axis, wherein a greater diameter of the second truncated cone is formed toward the first abutment surface;
   at least one positioning element;
   said at least one positioning element being rigid and being arranged on one of said first abutment surface and said guide opening surface;
   said at least one positioning element being configured to be received with form-fit engagement in a corresponding mating element on the surgical microscope;
   at least one holding element disposed in spaced relationship to said positioning element; and, said at least one holding element being configured to apply a holding force parallel to said first central axis between the protection glass adapter and the surgical microscope upon said at least one positioning element being received in said corresponding mating element on said surgical microscope, wherein the holding force is formed by a magnetic force.

2. The protection glass adapter of claim 1, wherein said at least one positioning element has a hemispherical shape.

3. The protection glass adapter of claim 1, wherein two positioning elements are arranged on said first abutment surface or on said guide opening surface.

4. The protection glass adapter of claim 1, wherein three positioning elements are arranged on said first abutment surface or on said guide opening surface.

5. The protection glass adapter of claim 1, wherein said at least one holding element includes at least two holding elements.

6. The protection glass adapter of claim 1, wherein said guide opening has a cone angle lying in a range between 10° and 45°.

7. The protection glass adapter of claim 1, wherein said guide opening has a cone angle lying in a range between 10° and 20°.

8. The protection glass adapter of claim 1 further comprising an objective protection glass.

9. The protection glass adapter of claim 8 further comprising:
a receiving device configured to receive said objective protection glass; and,
said objective protection glass being configured to separably connect to the protection glass adapter.

10. The protection glass adapter of claim 1 further comprising a microscope drape arranged on the protection glass adapter.

11. The protection glass adapter of claim 10, wherein said microscope drape is arranged on said first abutment surface.

12. The projection glass adapter of claim 1, wherein said guide opening surface is a smooth uninterrupted surface.

13. A surgical microscope comprising:
a main objective defining an outer circumferential surface thereof;
a protection glass adapter having a first abutment surface;
the surgical microscope defining a second abutment surface;
said first and said second abutment surfaces being configured to be brought into contact with each other;
said protection glass adapter defining a guide opening configured to receive said main objective;
said guide opening having a guide opening surface and being adapted as a truncated cone with a first central axis, wherein a greater diameter of the truncated cone is formed toward the first abutment surface;
at least one positioning element;
said at least one positioning element being rigid and being arranged on one of said first abutment surface and said guide opening surface;
at least one mating positioning element which, in position and shape, is configured to form-fit engage with said at least one positioning element upon said at least one positioning element and said at least one mating positioning element being brought into alignment with each other;
at least one holding element disposed in spaced relationship to said at least one positioning element;
said at least one holding element being configured to apply a holding force parallel to said first central axis between the protection glass adapter and the surgical microscope upon said at least one positioning element being received in said at least one mating positioning element, wherein the holding force is formed by a magnetic force;
said outer circumferential surface of said main objective being configured as a second truncated cone, wherein the greater diameter of the second truncated cone of said main objective is formed toward the second abutment surface of said surgical microscope; and,
at least one mating holding element configured to coact with said at least one holding element to effect said magnetic force between said at least one holding element and said at least one mating holding element upon said at least one positioning element being received in said at least one mating positioning element.

14. The surgical microscope of claim 13, wherein:
said guide opening of the protection glass adapter is guided over said main objective;
said protection glass adapter is configured to be movable in a rotary motion about said first central axis when said at least one positioning element is in contact with said second abutment surface, such that said first abutment surface is arranged by the positioning element at a distance from the second abutment surface when said at least one positioning element is not positioned in form-fit engagement with said mating positioning element; and,
said holding force between said at least one holding element and said at least one mating holding element is formed exclusively at a first position at which said at least one positioning element is positioned at a predetermined position in relation to the surgical microscope and said at least one positioning element is arranged in form-fit engagement in said mating positioning element in relation to the surgical microscope, such that said first abutment surface is in contact with the corresponding second abutment surface exclusively at said first position.

15. A surgical microscope comprising:
a main objective configured as a first truncated cone;
a protection glass adapter having a first abutment surface;
the surgical microscope defining a second abutment surface;
said first and said second abutment surfaces being configured to be brought into contact with each other to conjointly define a contact interface;
said main objective having a greater diameter formed toward said contact interface;
said protection glass adapter defining a guide opening configured to receive said main objective;
said guide opening having a guide opening surface and being configured as a second truncated cone with a central axis, wherein a greater diameter of the second truncated cone is formed toward contact interface;
a positioning element;
said positioning element being rigid and being arranged on one of said abutment surfaces;
a mating positioning element arranged on the other one of said abutment surfaces;
said mating positioning element being, in position and shape, configured to form-fit engage with said positioning element upon said positioning element and said mating positioning element being brought into alignment with each other as a consequence of a rotation of said protection glass adapter about said central axis;

a holding element disposed in spaced relationship to said positioning element;

said holding element being arranged on one of said abutment surfaces and being configured as a permanent magnet to apply a magnetic holding force parallel to said central axis between the protection glass adapter and the surgical microscope upon said positioning element being received in said mating positioning element;

a mating holding element made of ferromagnetic material arranged on the other one of said abutment surfaces in spaced relationship to said mating positioning element; and, said mating holding element being in abutment with said permanent magnet to coact therewith to effect said magnetic holding force between said holding element and said mating holding element when said positioning element is received in said mating positioning element.

\* \* \* \* \*

UNITED STATES PATENT AND TRADEMARK OFFICE
CERTIFICATE OF CORRECTION

PATENT NO. : 10,156,718 B2
APPLICATION NO. : 15/376300
DATED : December 18, 2018
INVENTOR(S) : F. Koenig et al.

It is certified that error appears in the above-identified patent and that said Letters Patent is hereby corrected as shown below:

In the Claims

In Column 12:
Line 56: insert -- said -- before "contact interface;".

Signed and Sealed this
Twenty-fifth Day of June, 2019

Andrei Iancu
*Director of the United States Patent and Trademark Office*